United States Patent [19]
Owens

[11] Patent Number: 5,036,850
[45] Date of Patent: Aug. 6, 1991

[54] BIPHASIC PULSE OUTPUT STAGE FOR ELECTRONIC STIMULATING DEVICE

[75] Inventor: Alan R. Owens, Longmont, Colo.

[73] Assignee: Staodyn, Inc., Longmont, Colo.

[21] Appl. No.: 398,750

[22] Filed: Aug. 25, 1989

[51] Int. Cl.[5] .............................................. A61N 1/08
[52] U.S. Cl. ................................ 128/421; 128/423 W
[58] Field of Search ................... 128/421, 423, 423 W, 128/422, 419 D

[56] References Cited

U.S. PATENT DOCUMENTS

| | | | |
|---|---|---|---|
| 2,375,575 | 5/1945 | Morland et al. | 128/421 |
| 3,563,247 | 2/1971 | Bowers | 128/422 |
| 3,924,641 | 12/1975 | Weiss | 128/419 PG |
| 3,946,745 | 3/1976 | Hsiang-Lai et al. | 128/421 |
| 4,237,899 | 12/1980 | Hagfors et al. | 128/422 |
| 4,256,116 | 3/1981 | Meretsky et al. | 128/421 |
| 4,632,117 | 12/1986 | James | 128/421 |
| 4,640,286 | 2/1987 | Thomson | 128/421 |
| 4,803,988 | 2/1989 | Thomson | 128/421 |
| 4,813,418 | 3/1989 | Harris | 128/421 |

FOREIGN PATENT DOCUMENTS 0280526 8/1988 European Pat. Off. ........ 128/419 D

Primary Examiner—William E. Kamm
Assistant Examiner—Scott M. Getzow
Attorney, Agent, or Firm—Robert E. Harris

[57] ABSTRACT

A biphasic pulse output stage is disclosed for an electronic stimulating device, such as a transcutaneous nerve stimulating device capable of effecting suppression of pain by nerve fiber stimulation. Biphasic constant current output pulses are applied to a user through an electrode pair noninvasively positioned at the skin of the user. Microprocessor generated control pulses control generation of the biphasic output pulses at one or more biphasic output stages each of which is associated with an electrode pair, and the generated biphasic output pulses are capacitively coupled from each output stage which also includes a bleeder network for effecting capacitor discharge.

20 Claims, 7 Drawing Sheets

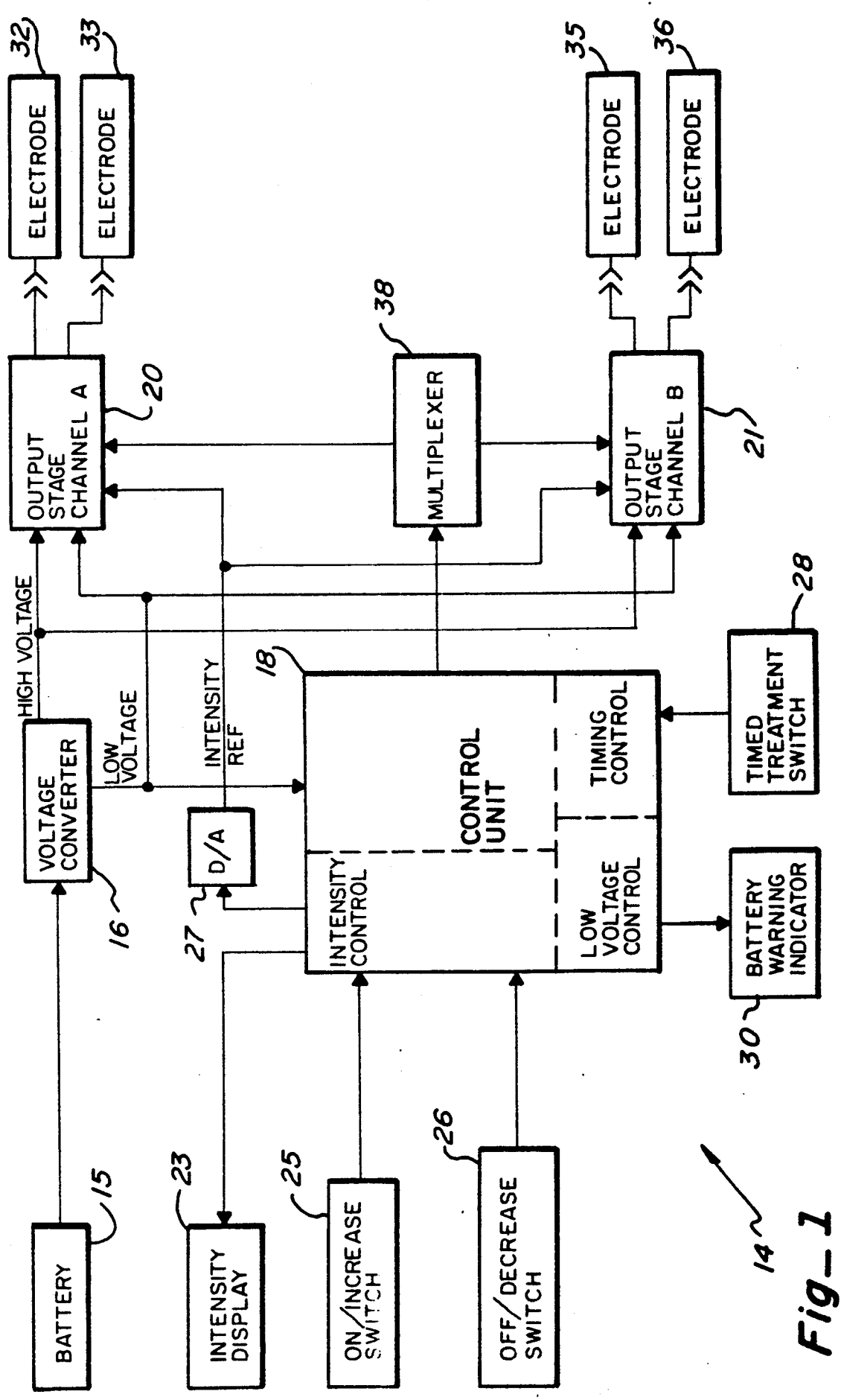
Fig_1

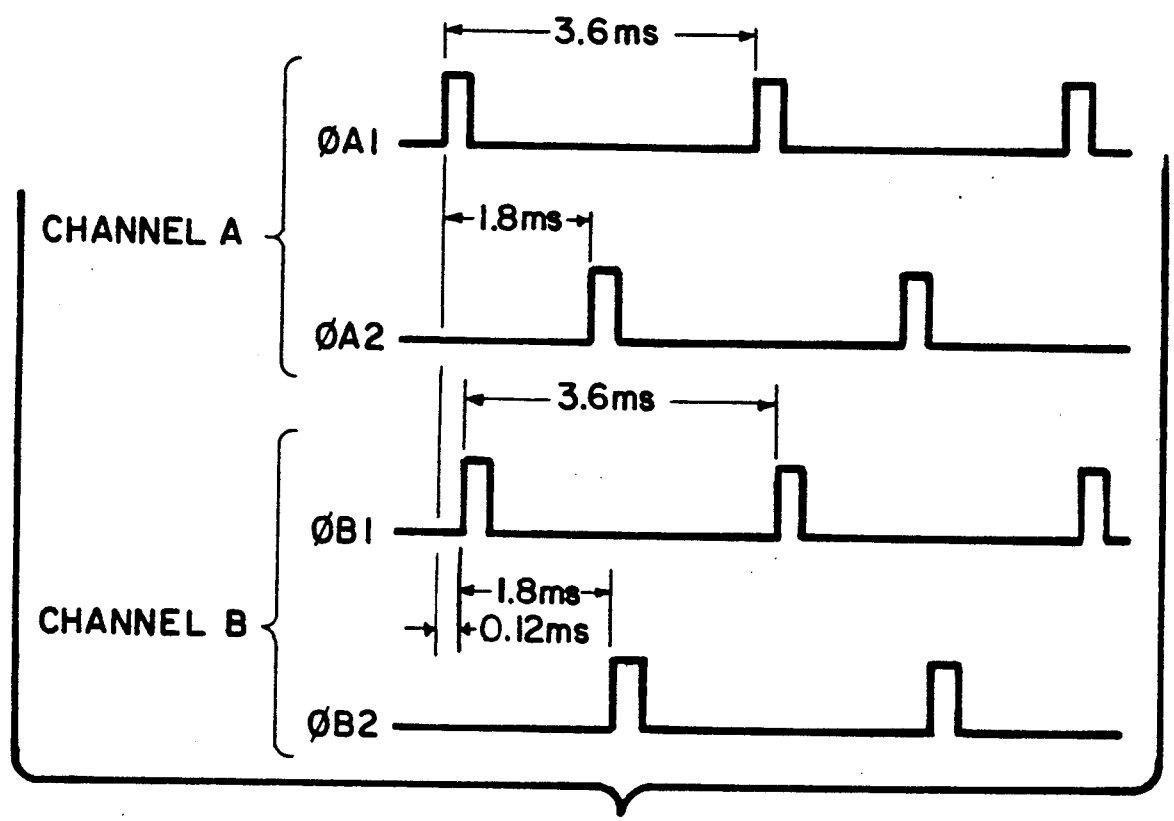
Fig_2
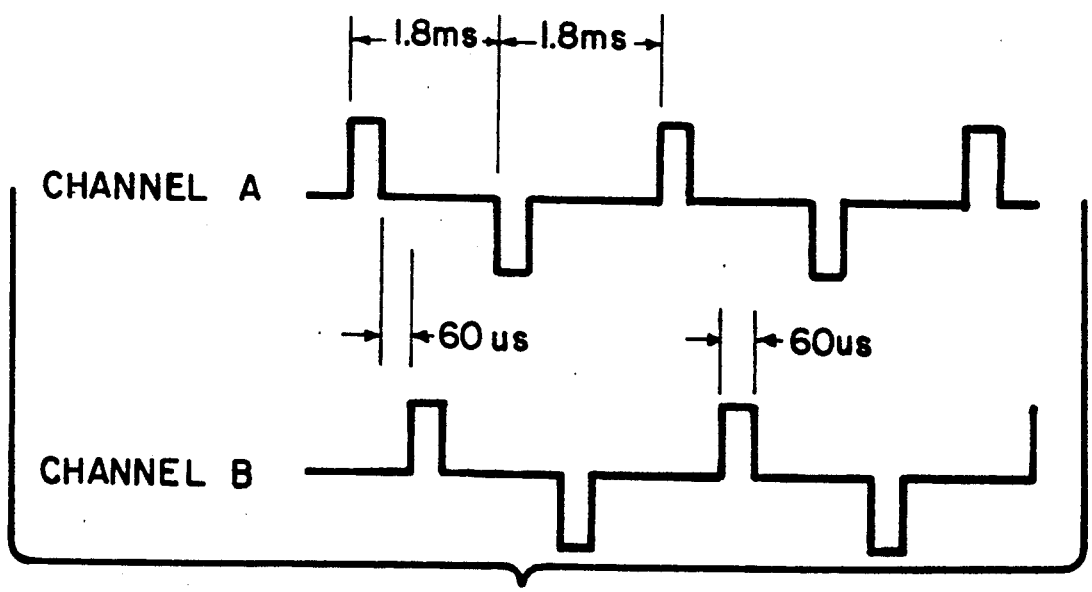
Fig_3

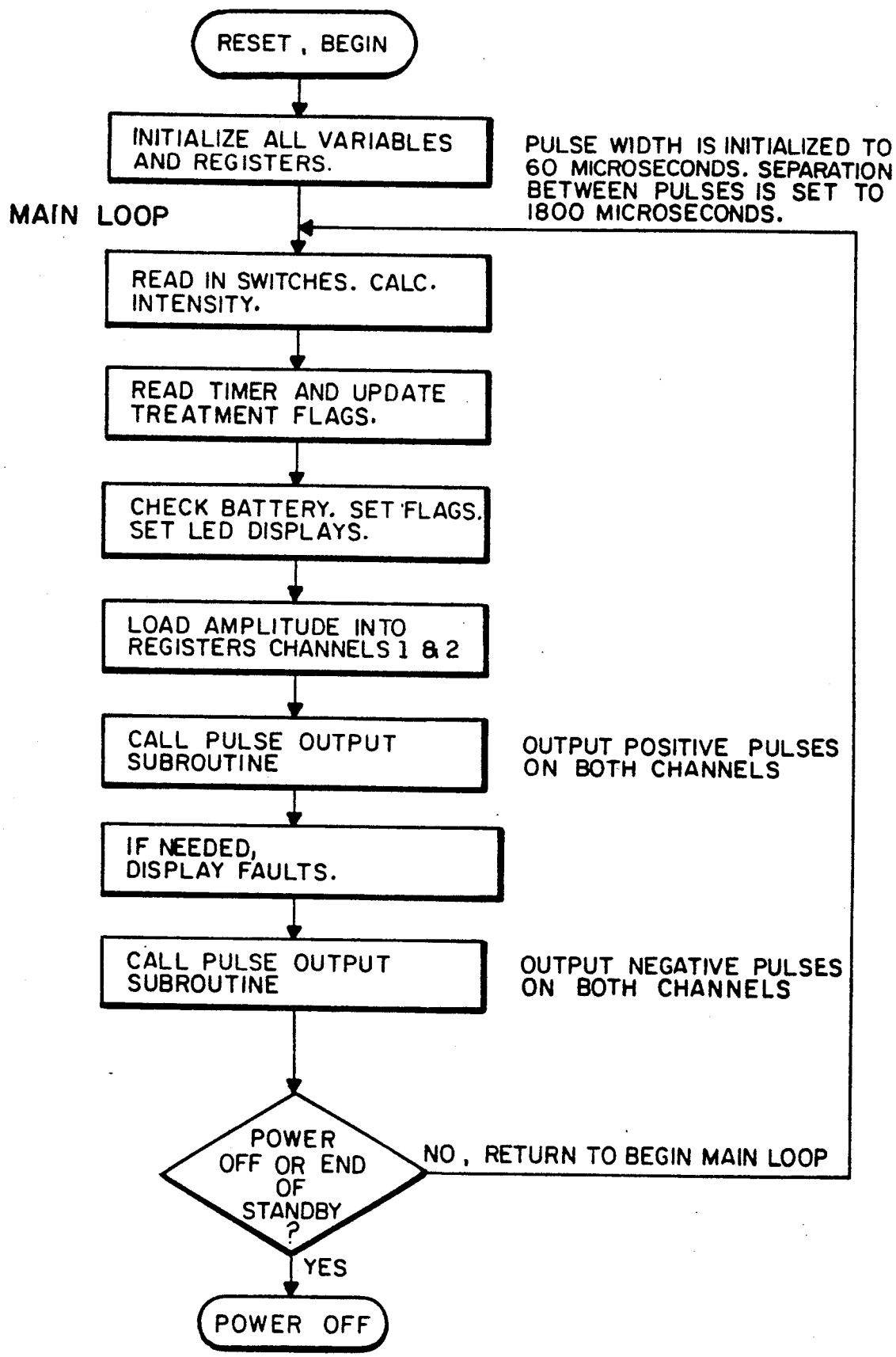
Fig_4A

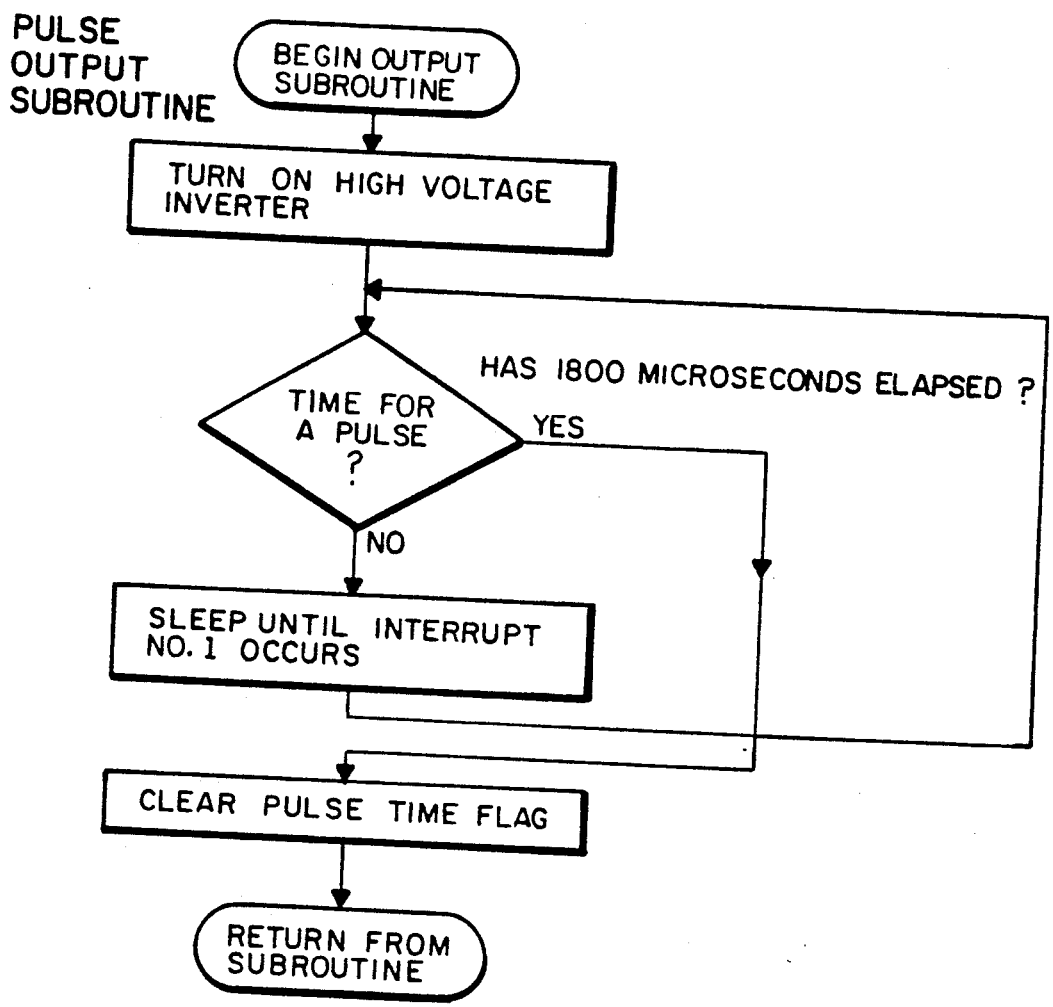
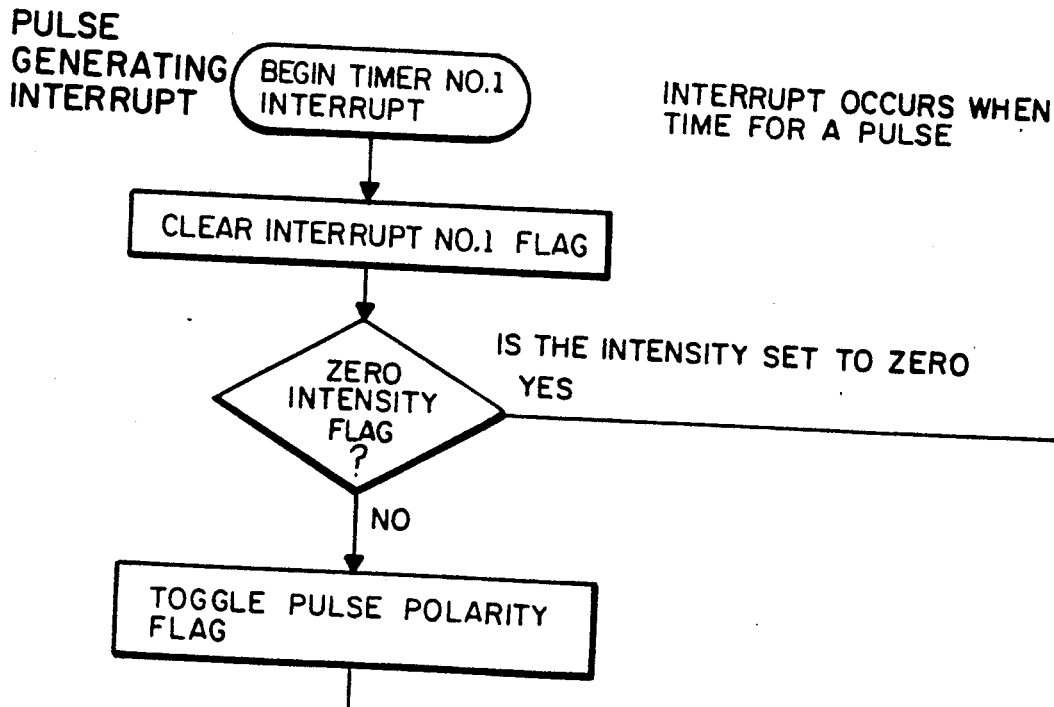
Fig_4B

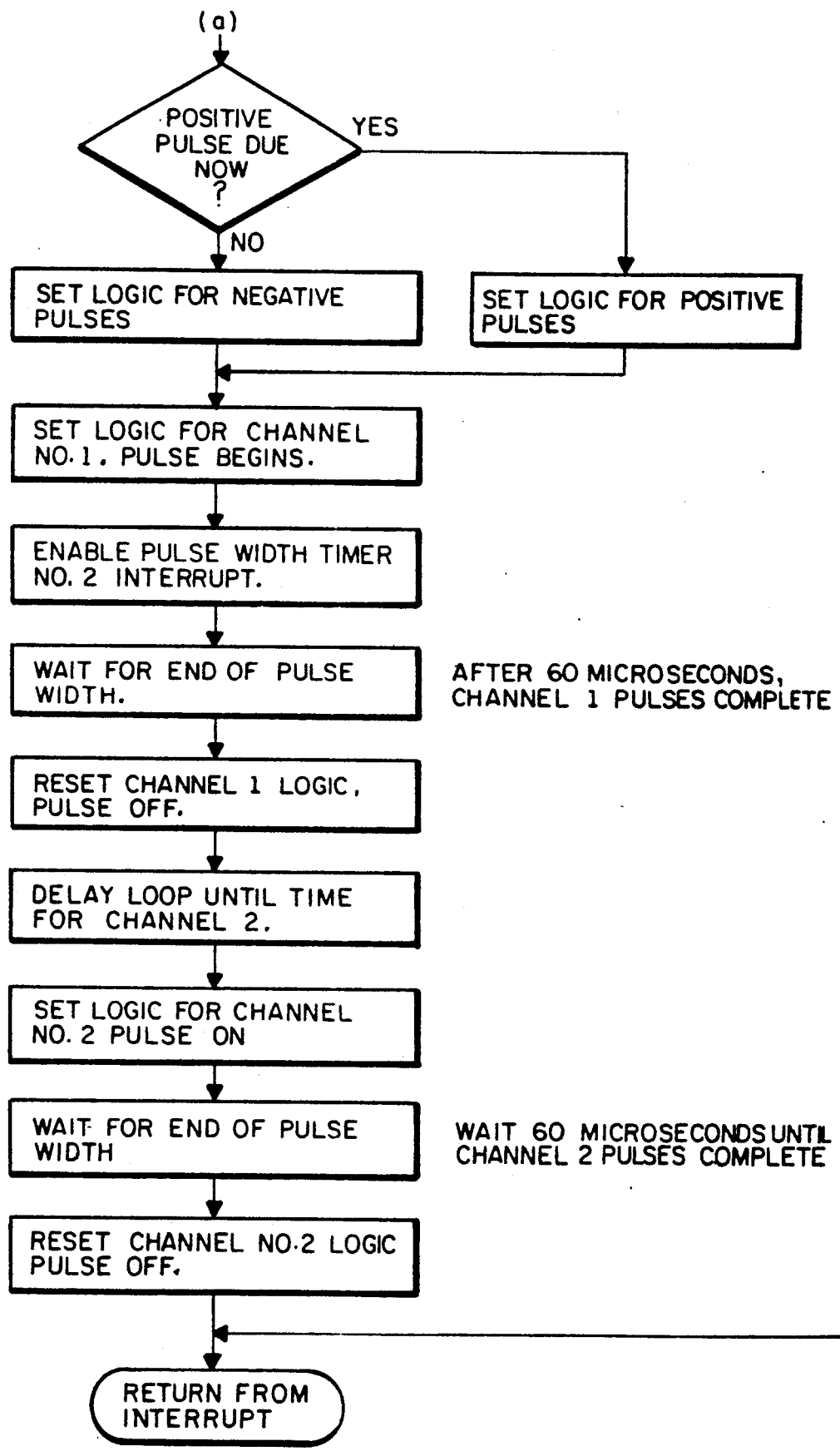
Fig_4C

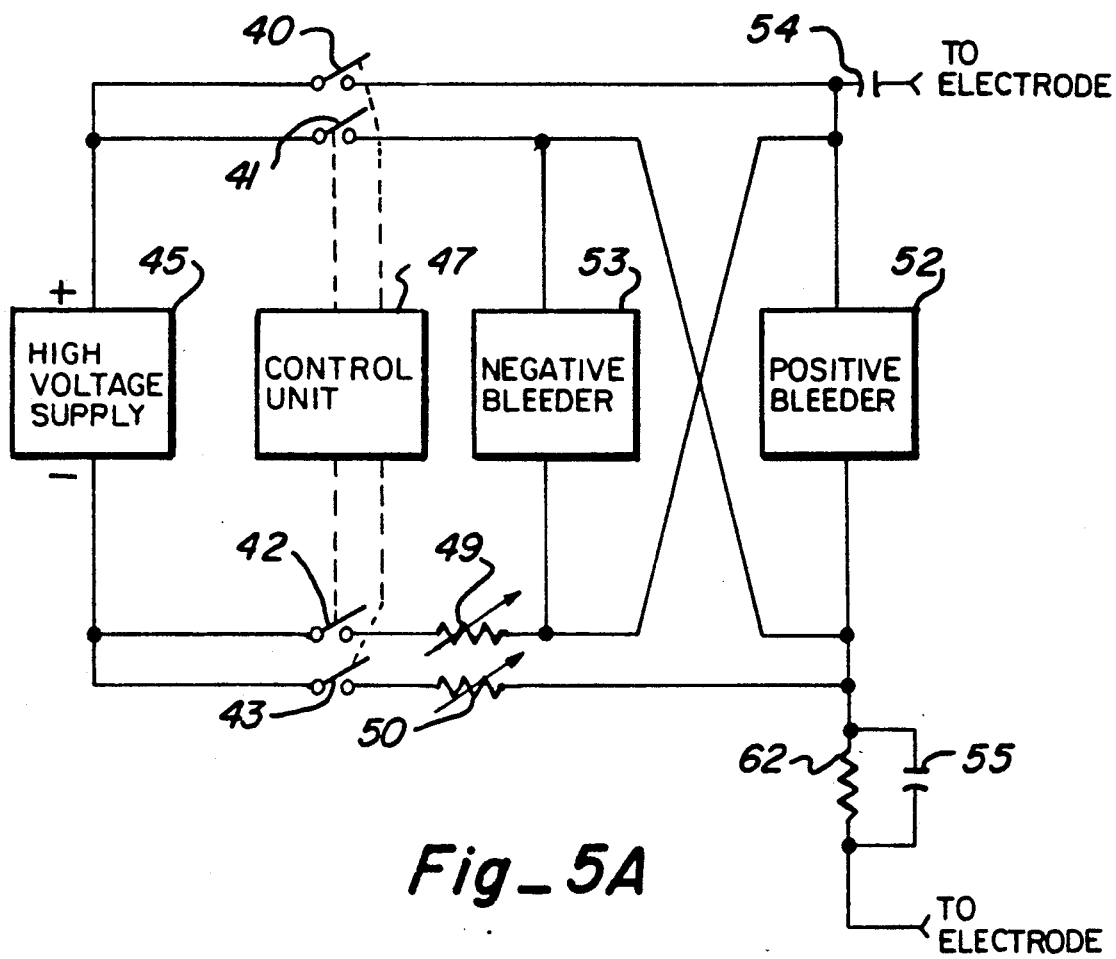
Fig_5A
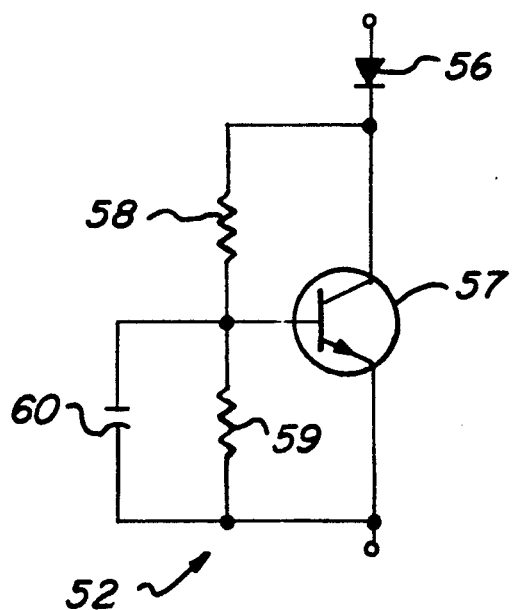
Fig_5B

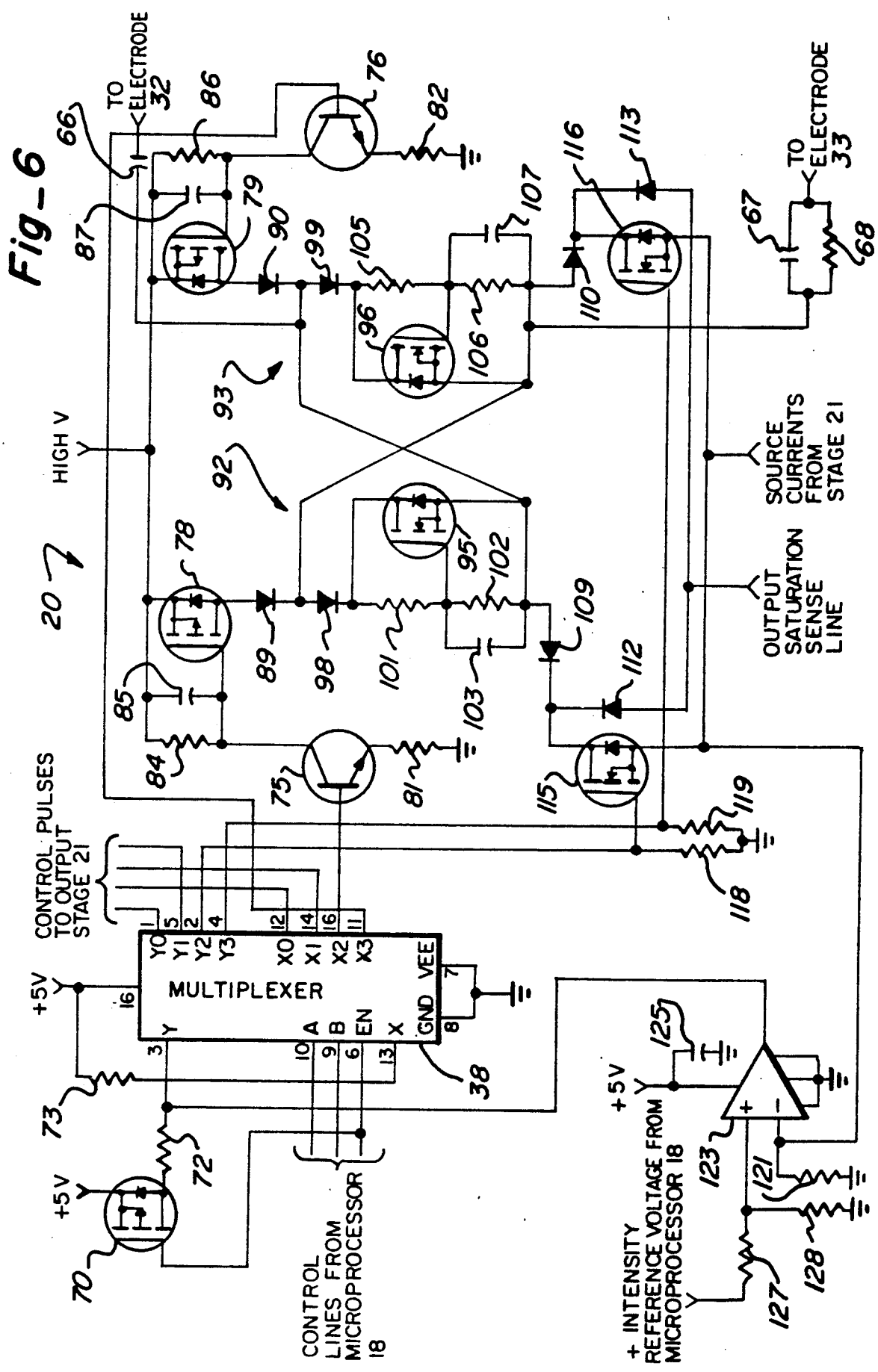

BIPHASIC PULSE OUTPUT STAGE FOR ELECTRONIC STIMULATING DEVICE

FIELD OF THE INVENTION

This invention relates to an electronic stimulating device, and, more particularly, relates to an electronic stimulation device, such as a transcutaneous nerve stimulating (TENS) device, having one or more biphasic pulse output stages.

BACKGROUND OF THE INVENTION

The use of electronic stimulating devices are now well known, and examples of such devices to suppress pain are also now well known (see, for example, in U.S. Pat. Nos. 4,014,347, 4,210,150 and 4,632,117).

More recently, it has been found that biphasic pulses can be used to good advantage in connection with electronic stimulating devices, and examples of devices generating biphasic pulses are shown, for example, in U.S. Pat. Nos. 2,375,575 3,946,745, 4,237,899 and 4,256,116.

Still more recently, it has been found that specific groupings of biphasic pulses can be used to increase the activity of selected nerve fibers (see U.S. Pat. No. 4,640,286). It has also been found that specific groupings of biphasic pulses can be used to good advantage with plural equally active electrodes (see U.S. Pat. No. 4,803,988), and, more particularly, with symmetrical biphasic pulses applied through equally active electrodes to one or more channels (see U.S. Pat. No. 4,813,418).

Transcutaneous nerve stimulating devices providing dual channel isolation and including capacitively coupled outputs with associated bleeder circuitry have also heretofore been suggested for use with monopolar-type stimulation (see, for example, U.S. Pat. No. 4,632,117 wherein a high voltage power supply is connected to the electrodes by transistor switches controlled by control pulses provided thereto by a pulse generator, with the power supply being isolated from the user by a capacitor/diode arrangement so that the device cannot directly deliver any net DC charge to the user, and with a bleeder resistor that discharges the output capacitor during the intervals between the pulses).

Thus, while electronic stimulating devices, including transcutaneous nerve stimulating devices, have been heretofore suggested, and while such devices have heretofore been extensively modified, additional improvements can still be utilized to good advantage.

SUMMARY OF THE INVENTION

This invention provides an improved biphasic pulse output stage, or stages, for an electronic stimulating device, and, more particularly, for a transcutaneous nerve stimulating (TENS) device that provides a biphasic pulse output for effecting pain suppression.

The device includes a control unit, which can be a microprocessor control unit, for generating control pulses that are provided to one or more output stages, or channels, along with high voltage so that each output stage generates biphasic output pulses, which pulses are coupled from each output stage, preferably by capacitive coupling having bleeder circuitry connected therewith, for application to a user through an electrode pair noninvasively positioned at the skin of the user.

It is therefore an object of this invention to provide an improved electronic stimulating device that includes an improved biphasic pulse output stage or stages.

It is another object of this invention to provide an improved transcutaneous nerve stimulating device as the electronic stimulating device that includes an improved biphasic pulse output stage or stages.

It is still another object of this invention to provide an improved electronic stimulating device that includes one or more output stages providing a biphasic pulse output through capacitive coupling having bleeder circuitry connected therewith.

It is still another object of this invention to provide an improved output stage, or stages, for an electronic stimulating device.

With these and other objects in view, which will become apparent to one skilled in the art as the description proceeds, this invention resides in the novel construction, combination, and arrangement of parts substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 is a block diagram illustrating an electronic stimulating device, which device is illustrated as a transcutaneous nerve stimulating device, and which device includes a pair of biphasic pulse output stages;

FIG. 2 illustrates typical control pulses provided by the control unit to control generation of biphasic output pulses at the dual output stages as shown in FIG. 1;

FIG. 3 illustrates typical biphasic pulse outputs coupled from the dual output stages as shown in FIG. 1;

FIGS. 4A through 4C, taken together, form a flow chart for generation of control pulses using a microprocessor as the control unit;

FIG. 5A is a simplified illustration of a capacitively coupled output stage providing a biphasic pulse output;

FIG. 5B is a schematic diagram illustrating the bleeder circuitry shown in block form in FIG. 5A; and FIG. 6 is a schematic diagram of a now preferred capacitively coupled output stage providing a biphasic pulse output.

DESCRIPTION OF THE INVENTION

An electronic stimulating device, and more particularly, a transcutaneous nerve stimulating device 14, is shown by the block diagram of FIG. 1. As shown, battery 15 is utilized as the sole power source to power device 14. Battery 15, preferably a 9 volt battery, is connected with conventional voltage converter, or inverter, 16, and converter 16 supplies a low voltage DC output, preferably 5 volts, to control unit 18, as well as to output stages, or channels, 20 and 21. In addition, converter 16 also supplies a high voltage DC output preferably 100 volts maximum, to output stages 20 and 21.

Control unit 18 can include an intensity display 23 connected therewith, with the intensity being selected by intensity on/increase switch 25 and intensity off/decrease switch 26, both of which are externally actuatable. As also indicated, an intensity reference (the level of which is selected using intensity switches 25 and 26 in conjunction with the intensity control provided by control unit 18) is supplied by control unit 18, converted to analog form, if necessary, in digital-to-analog (D/A) converter 27, and then coupled to output stages 20 and 21.

Control unit 18 can also provide a timing control that is activated by timed treatment switch 28. In addition, control unit 18 can include a low voltage control with detected low battery voltage being indicated at battery warning indicator 30.

Output stage 20 (channel A, or 1, as also referred to herein) is connectable with electrodes 32 and 33, providing a first electrode pair, and output stage 21 (channel B, or 2, as also referred to herein) is connectable with electrodes 35 and 36, forming a second electrode pair.

Control unit 18 generates control pulses, as typically shown in FIG. 2, with the control pulses designated for channel A being coupled through multiplexer 38 to output stage 20, and with the control pulses designated for channel B being coupled through multiplexer 38 to output stage 21, to control generation of the biphasic pulse outputs at each output stage, or channel, as typically shown in FIG. 3.

A more detailed explanation of the control pulses, as well as the biphasic pulse output to be provided, is set forth U.S. Pat. No. 4,813,418, which is hereby incorporated herein by reference. Control unit 18 may include a microprocessor and a flow chart for pulse generation using a microprocessor is shown in FIGS. 4A through 4C. Apparatus for producing control pulses, such as shown and described in U.S. Pat. No. 4,813,418, could also be utilized to generate the control pulses.

A biphasic output stage requires circuitry that enables generation of pulses having both positive and negative polarities. As indicated by the simplified schematic diagram of FIG. 5A, this can be accomplished using four transistor switches 40, 41, 42 and 43. Switches 40 and 41 are gate on/off transistors that connect high voltage supply 45 to an electrode pair (such as, for example, by providing high voltage from converter 16 to electrodes 32 and 33, as indicated in FIG. 1) at different times. The transistors are turned-on by control pulses supplied thereto from control pulse generator 47 (which pulses can be generated, for example by control unit 18, as indicated in FIG. 1) with the control pulses provided being as indicated, for example, in FIG. 2 (it being realized that the pulse spacing between channels could be varied, as, for example, utilizing 180 ms between occurrences of like pulses in different channels as is now preferred in some TENS devices now provided).

Switches 42 and 43 functionally include variable resistance represented in FIG. 5A as variable resistors 49 and 50 connected in series therewith and these transistors serve both as switches and current level control variable resistors. When not turned on by a control pulse, the transistors are off and have infinite resistance. When a biphasic pulse output is produced (such as shown in FIG. 3, for example), conductance is determined by a voltage reference that sets the desired level of current for the pulses. Since variable-resistor/switch transistors 42 and 43 are connected to opposite electrodes, they cannot be combined and must be separate transistors that are turned on at different times by control pulses.

Positive and negative bleeder networks, or circuits, 52 and 53 discharge any voltage that may appear across output capacitors 54 and 55 (used to capacitively couple the output pulses from the device to the associated electrodes). If the two polarities of the output stage are perfectly balanced, the pulses generated can contain precisely the same charge and there would be no need for bleeder circuits, but this, most often, does not occur.

Positive bleeder circuit 52 is shown in schematic form in FIG. 5B (negative bleeder circuit 53 is identical to positive bleeder circuit 52 and has not been specifically illustrated). As shown in FIG. 5B, positive bleeder circuit 52 includes diode 56 (connected to one side of capacitor 54), transistor 57, resistor 58 and an RC network (consisting of parallel connected resistor 59 and capacitor 60) for transistor turn-on (negative bleeder circuit 53 has the diode connected to one side of capacitor 55). Such a bleeder circuit turns on slightly whenever the voltage on the gate rises sufficiently to turn on the transistor. As soon as this voltage has charged the capacitor across the base of the bleeder transistor, the bleeder transistor will turn on sufficiently for capacitor discharge.

When two output capacitors (such as capacitors 54 and 55) are used, however, there is no complete DC path around the circuit to fully discharge the capacitors. If the capacitors become equally charged to a sufficient voltage, while for example 20 volts, circuits 52 and 53 would ensure that the voltages across these two capacitors were equal, circuits 52 and 53 could not actually dissipate the accumulated charge unless a DC path is provided.

In practice, charge sometimes gathers in these capacitors. This is important because small, compact ceramic capacitors lose their capacitance when the voltage across them is high. This causes the output pulses to have sloping top portions and even greater voltage across the capacitors. The charge problem is effectively corrected by including a high resistance shunt 62 across one of the two output capacitors, as illustrated in FIG. 5A. Only one of the output capacitors is shunted so that one capacitor remains in the output current path to ensure that the net DC delivered to the patient will be zero.

The skin of a user between spaced electrodes appears as a complex RC network which illustrates that, although the ohmic resistance path across the tissue may be high, it is nevertheless an ohmic path that can conduct DC charge around a circuit path to discharge both capacitors 54 and 55.

A bleeder circuit, such as shown in FIG. 5B, has another function. If the pulse width should become very long and/or the pulse amplitude should become very high, the bleeder circuit will turn on hard and actually short out the voltage across the two electrodes. This function serves as a safety device in the event that the logic circuitry fails and produces extremely long turn-on control pulses.

While a bleeder circuit such as illustrated in FIG. 5B can also include a diode positioned between the junction of resistor 59 and capacitor 60 and the junction of transistor 57 and electrode 33, such a diode operates, at least in part, as a clamp, and has been found to be undesirable for use with a biphasic output stage because a spike of current (handled by such a diode) will destroy the interphase delay that is necessary in the output stage.

A now preferred biphasic output stage is shown in FIG. 6, along with multiplexer 38. While only output stage 20 is shown, it is to be realized that output stage 21, as shown in FIG. 1, is preferably identical and is likewise connected with multiplexer 38.

As shown, output stage 20 includes capacitors 66 and 67 for capacitance coupling of the biphasic output pulses to electrodes 32 and 33, and capacitor 67 has a shunt resistor 68 connected thereacross. Control pulses are supplied to the output stage from microprocessor control unit 18 through multiplexer 38 which supplies control pulse outputs to both output stages 20 and 21.

Multiplexer 38 has a field effect transistor (FET) 70 connected with the enable control pulse input, has a resistor 72 connecting the drain of FET 70 to the Y input, and has a resistor 73 connecting the X input with the 5 volt power supply. The 5 volt level supplied to the multiplexer through the X input is used to switch on to transistors 75 and 76.

The control pulses from the X2 and X3 outputs of multiplexer 38 (for channel A) are coupled to transistor 75 and 76 for level translation and signal inversion to ensure proper operation of the gate transistors (field effect transistors 78 and 79 as shown in FIG. 5). As indicated, transistors 75 and 76 have their emitters connected with ground through resistors 81 and 82 (to supply a fixed voltage drive to the associated FET despite changes in the high voltage supply), FET 78 has parallel connected resistor 84 and capacitor 85 connecting the gate of the FET with the high voltage (from converter 16) to turn off FET 78 when transistor 75 turns off, and FET 79 has parallel connected resistor 86 and capacitor 87 connecting the gate of the FET with the high voltage to turn off FET 79 when transistor 76 turns off. In addition, FETs 78 and 79 have diodes 89 and 90 connected in series with the drain of the FET to protect the FETs from conducting in the reverse direction.

As also shown in FIG. 6, output stage 20 includes dual transistorized bleeder circuits 92 and 93 that are polarized, and therefore operate properly only in one direction. Field effect transistors 95 and 96 are used in these circuits and each contains an internal shunt diode that makes them appear a short circuit when they are reverse biased. As shown, FET 95 of bleeder circuit 92 has a series connected diode 98 that prevents reverse currents from flowing, and FET 96 of bleeder circuit 93 has a series connected diode 99 that prevents reverse currents from flowing.

In addition, bleeder circuit 92 has resistor 101 and an RC circuit, consisting of resistor 102 connected in parallel with capacitor 103, connected with FET 95, and bleeder circuit 93 has resistor 105 and an RC circuit, consisting of resistor 106 connected in parallel with capacitor 107, connected with FET 96.

As also shown, FET 95 has a diode 109 connected in series with the source of FET 95, while FET 96 has a diode 110 connected in series with the source of FET 96.

Output stage, or channel, 20 is designed to operate in conjunction with output stage, or channel, 21. When one channel is operating, it is important that the other channel does not provide a return path to the high voltage supply or ground. This would destroy the isolation because currents would appear at electrodes without the direct control of the control pulses that is supposed to completely determine the currents at each electrode.

Primary isolation is provided by the timing of the control pulses. A two channel device providing biphasic stimulation of each channel has two biphasic output stages each of which is connectable to a pair of electrodes. Each stage is separately driven by control pulse pairs that are separated in time from the control pulses of the other channels, as shown in FIG. 2.

Monitoring diodes 112 and 113 are connected with variable-resistor/switch FETs 115 and 116 (which also have resistors 118 and 119 to ground connected therewith) so that these diodes are used to detect when the drain voltages of the transistors are approaching saturation. These signals are used to boost the high voltage to keep the transistors out of saturation and the stimulator operating at maximum energy efficiency.

As shown, diodes 112 and 113 are connected between the FET (115 or 116) and the associated series protection diode (109 or 110), which diode prevents the associated FET from operating in the reverse direction. By this connection, the diodes cannot be forward biased by the opposite channel turning on, which would cause the high voltage supply to produce maximum voltage at all times.

Each output stage generates constant current rectangular biphasic output pulses. The source currents from all four intensity level control transistors (FETs 115 and 116 of output stage 20 as shown in FIG. 5 and like FETs for output stage 21) are brought together and passed through a common source to ground connected resistor 121. Since the currents through each half output stage are on at different times, the signals that appear across sense resistor 121 are unique for each half output stage.

The voltage across sense resistor 121 is fed to the negative input of operational amplifier 123 (a constant current amplifier that is connected with the 5 volt power supply with a by-pass capacitor 125 to ground connected thereto). The positive input to operational amplifier 123 is a reference voltage signal that represents the current level to be generated by the user (and could be provided through a potentiometer, but is preferably generated by a digital-to-analog converter, as indicated in FIG. 1) with the reference voltage being coupled to the positive input through resistor 127 having a resistor 28 to ground connected therewith. The amplifier is stable because feedback from the output current is negative and causes the negative input voltage to become equal to (or at least closely approach) the positive reference voltage input. The output from operational amplifier 123 is coupled to the Y input of multiplexer 38. FET 70 and resistor 72 comprise a pull-up to improve the positive drive of operational amplifier 123.

In operation, the user turns on the device by depressing briefly on/increase intensity switch 25. The user then adjusts the intensity to the desired degree of stimulation by depressing either on/increase switch 25 or off/decrease switch 26 and observing the LED light array at intensity display 23. For continuous stimulation this is all that is necessary until treatment is terminated by decreasing stimulation to minimum (zero) by actuating off/decrease switch 26 until all display LED lights are off. For a timed treatment, timed treatment switch 28 is depressed to start a timed cycle.

As can be appreciated from the foregoing, this invention provides an improved output stage useful in an electronic stimulating device and, more particularly, an improved transcutaneous nerve stimulating device, to provide one ore more biphasic pulse output stages.

What is claimed is:

1. An output stage unit for use in an electronic stimulating device having power supply means adapted to be connected with a power source for supplying a high voltage output and control means for providing timewise spaced control pulses, and including first and second electrodes, said output stage unit, comprising:
  biphasic pulse generating means connected with said power supply means and said control means and responsive to receipt of said high voltage and control pulses therefrom providing a biphasic pulse output;
  coupling means including capacitive means and having first and second outputs each of which is adapted to be connected with different ones of said first and second electrodes such that said first electrode provides a return path for said second electrode when said second electrode is active and said second electrode provides a return path for the first electrode when said first electrode is active, said biphasic pulse output being coupled to said first and second outputs through said capacitance coupling means; and
  bleeder means, including dual bleeder circuits, connected with said coupling means for discharging said capacitance means after said biphasic pulse output has been coupled therethrough.

2. The unit of claim 1 wherein each of said dual bleeder circuits includes resistance means having switching means connected therewith for controlling discharge of said capacitance coupling means through said resistance means.

3. The unit of claim 2 wherein said switching means in each of said dual bleeder circuits includes a field effect transistor.

4. The unit of claim 3 wherein each of said bleeder circuits includes an RC network connected with said field effect transistor for facilitating transistor turn on.

5. The unit of claim 3 wherein each of said bleeder circuits is connected with a second field effect transistor acting as a gate transistor in said biphasic pulse generating means.

6. The unit of claim 5 wherein each of said bleeder circuits is also connected with a third field effect transistor serving as a variable-resistor switch.

7. The unit of claim 6 wherein each of said first, second and third field effect transistors has a diode connected in series therewith to ensure operation of each said field effect transistor in only one direction.

8. The unit of claim 1 wherein said unit also includes intensity control means, and wherein said biphasic pulse generating means is connected with said intensity control means for controlling the intensity of said biphasic pulse output.

9. The unit of claim 8 wherein said intensity control means includes an operational amplifier.

10. The unit of claim 1 wherein said device includes a second output stage unit connected with said power supply means and said control means and, responsive to receipt of said high voltage and control pulses, providing a second biphasic pulse output.

11. The unit of claim 10 wherein said second output stage unit includes second capacitance coupling means having third and fourth outputs each of which is adapted to be connected with an electrode, with said second biphasic pulse output being coupled to said third and fourth outputs through said second capacitance coupling means, and with said second output stage unit also including second bleeder means having dual bleeder circuits connected with said second capacitance coupling means for discharging said second capacitance coupling means after said second biphasic pulse output has been coupled therethrough.

12. The unit of claim 1 wherein said electronic stimulating device is a transcutaneous nerve stimulating device, and wherein said biphasic pulse generating means provides a biphasic pulse output suitable for stimulating nerves of a user receiving said pulse output from electrodes connected with said capacitance coupling means.

13. In an electronic stimulating device having power supply means adapted to be connected with a power source for supplying a high voltage output and control means for providing timewise spaced control pulses, and including first and second electrodes an output stage unit, comprising:
  biphasic pulse generating means connected with said power supply means and said control means, said biphasic pulse generating means including first transistor means for receiving said control pulses and said high voltage and responsive thereto for providing a biphasic pulse output;
  coupling means, including capacitance means, for receiving said biphasic pulse output from said biphasic pulse generating means, said coupling means having first and second outputs each of which is adapted to be connected with different ones of said first and second electrodes such that said first electrode provides a return path for said second electrode when said second electrode is active and said second electrode provides a return path for the first electrode when said first electrode is active, and said biphasic pulse output being coupled to said first and second outputs through said capacitance means; and
  dual bleeder circuit means each of which includes resistance means and second transistor means for controlling discharge of said capacitance means after said biphasic pulse output has been coupled therethrough.

14. The unit of claim 13 wherein each of said dual bleeder circuit means includes an RC network connected with said second transistor means for facilitating transistor turn on.

15. The unit of claim 13 wherein said output stage unit includes a second biphasic pulse generating means comparable to said biphasic pulse generating means, a second coupling means comparable to said coupling means, and a second dual bleeder circuit means comparable to said dual bleeder circuit means, whereby said output stage unit provides a second capacitance coupled biphasic pulse output.

16. A dual output stage unit for an electronic stimulating device having power supply means for supplying a high voltage output and control means for supplying first and second sets of timewise spaced control pulses, said dual output stage unit, comprising:
  multiplexer means connected with said control means for providing said first set of timewise spaced pulses at one output and said second set of timewise spaced pulses at said a second output;
  first and second biphasic pulse generating means connected with said power supply means and said multiplexer means, said first biphasic pulse generating means receiving said high voltage output and said first set of control pulses and said second biphasic pulse generating means receiving said high voltage output and said second set of control pulses, and said first and second biphasic pulse generating means, responsive to receipt of said high voltage and said control pulses, each providing a biphasic pulse output the pulses of which are timewise spaced from the pulses of the other of said biphasic pulse output;

first and second output means each of which includes capacitance means, said first output means being connected with said first biphasic pulse generating means to receive said biphasic pulse output therefrom and capacitively couple said received biphasic pulse output therethrough, and said second output means being connected with said second biphasic pulse generating means to receive said biphasic pulse output therefrom and capacitively couple said received biphasic pulse output therethrough; and first and second bleeder means, each of which is connected with different ones of said first and second capacitance means for discharging said capacitance means after said biphasic pulse output has been coupled therethrough.

17. The unit of claim 16 wherein each of said first and second bleeder means includes dual bleeder circuits.

18. The unit of claim 16 wherein each of said dual bleeder circuits includes resistance means, transistor switching means connected with said resistance means to control the discharge of said associated capacitance means therethrough, and an RC network for facilitating turn on of said transistor switching means.

19. The unit of claim 18 wherein each of said transistor switching means is a field effect transistor having a diode connected in series therewith to ensure operation of each said field effect transistor in only one direction.

20. The unit of claim 16 wherein said electronic stimulating device is a transcutaneous nerve stimulating device, and wherein said first and second biphasic pulse generating means provide biphasic pulse outputs suitable for stimulating nerves of a user receiving said pulse outputs from electrodes connected with said first and second output means.

* * * * *